United States Patent [19]

Sutter

[11] Patent Number: 5,084,040

[45] Date of Patent: Jan. 28, 1992

[54] LYOPHILIZATION DEVICE

[75] Inventor: Steven T. Sutter, Spring City, Pa.

[73] Assignee: The West Company, Incorporated, Phoenixville, Pa.

[21] Appl. No.: 469,946

[22] Filed: Jan. 25, 1990

[51] Int. Cl.$^5$ .............................................. A61B 19/00
[52] U.S. Cl. ....................................... 604/403; 604/408; 604/415; 206/504; 428/35.7
[58] Field of Search ................ 206/504, 524.2, 822, 206/828; 428/34.7, 35.7; 604/232, 403–407, 411, 415, 416

[56] References Cited

U.S. PATENT DOCUMENTS

| | | | |
|---|---|---|---|
| 3,765,574 | 10/1973 | Urquiza | 206/504 |
| 3,926,341 | 12/1975 | Lhoest | 222/95 |
| 4,174,238 | 11/1979 | Fowles et al. | 156/69 |
| 4,258,847 | 3/1981 | Nierman | 206/504 |
| 4,533,578 | 8/1985 | Boyd et al. | 428/35.2 |
| 4,610,366 | 9/1986 | Estes et al. | 215/1 C |
| 4,657,133 | 4/1987 | Komatsu et al. | 206/204 |
| 4,700,838 | 10/1987 | Falciani et al. | 206/438 |
| 4,872,557 | 10/1989 | Ames | 206/504 |
| 4,886,504 | 12/1989 | Arvidson et al. | 604/257 |

FOREIGN PATENT DOCUMENTS

| | | | |
|---|---|---|---|
| 0299562 | 1/1989 | European Pat. Off. | 206/828 |
| 0326529 | 8/1989 | European Pat. Off. | 206/828 |
| 3082665 | 4/1988 | Japan | 206/828 |
| 1067314 | 1/1984 | U.S.S.R. | 206/828 |

*Primary Examiner*—John D. Yasko
*Assistant Examiner*—Adam J. Cermak
*Attorney, Agent, or Firm*—Eugene E. Renz, Jr.

[57] ABSTRACT

A lyophilization container device comprising a top end having at least one lyophilization port axially extending upward and defining a generally polygonally oval shape. The device includes a bottom end having generally the same shape as the top and having preferably a substantially flat bottom. Also included is a wall portion sealed to the top and bottom end to define the container, with the wall portion having an inside surface which is drug compatible and has sufficient buckle strength to withstand vertical force during stopper seating.

44 Claims, 3 Drawing Sheets

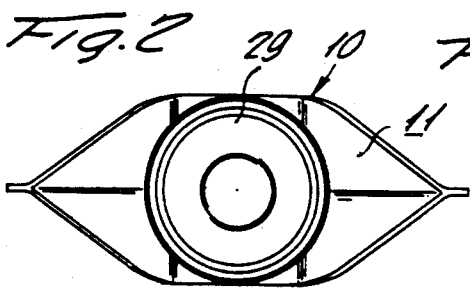
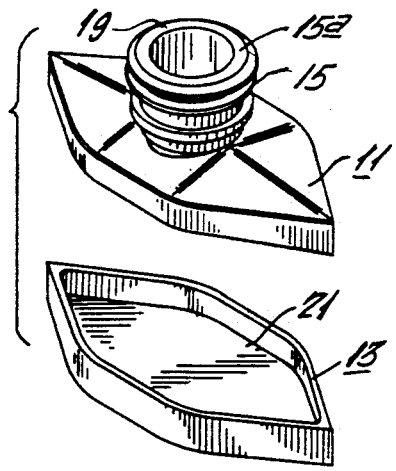
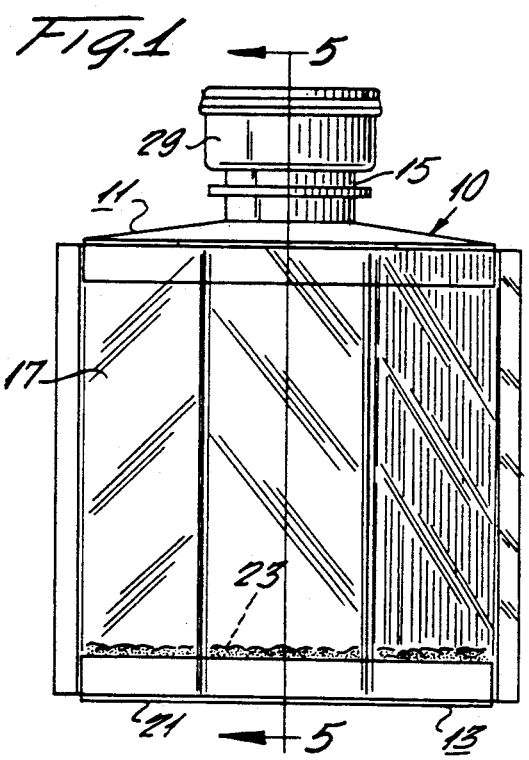
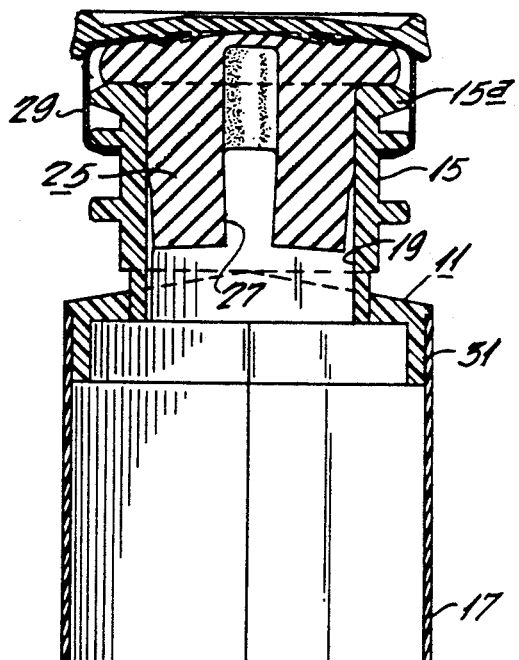
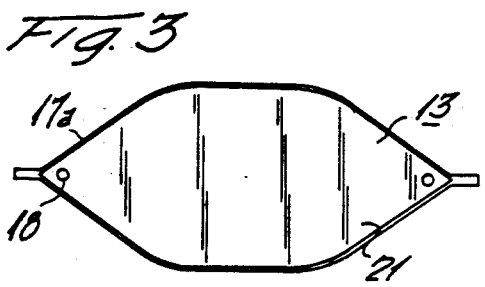
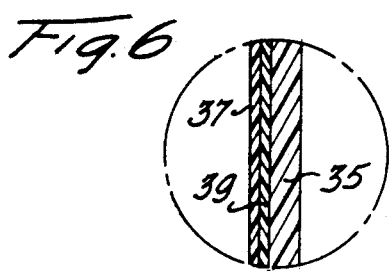
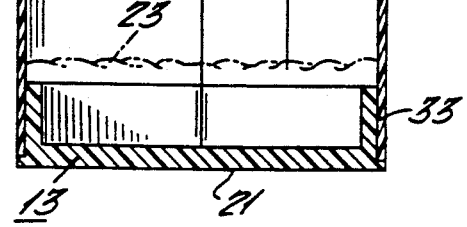

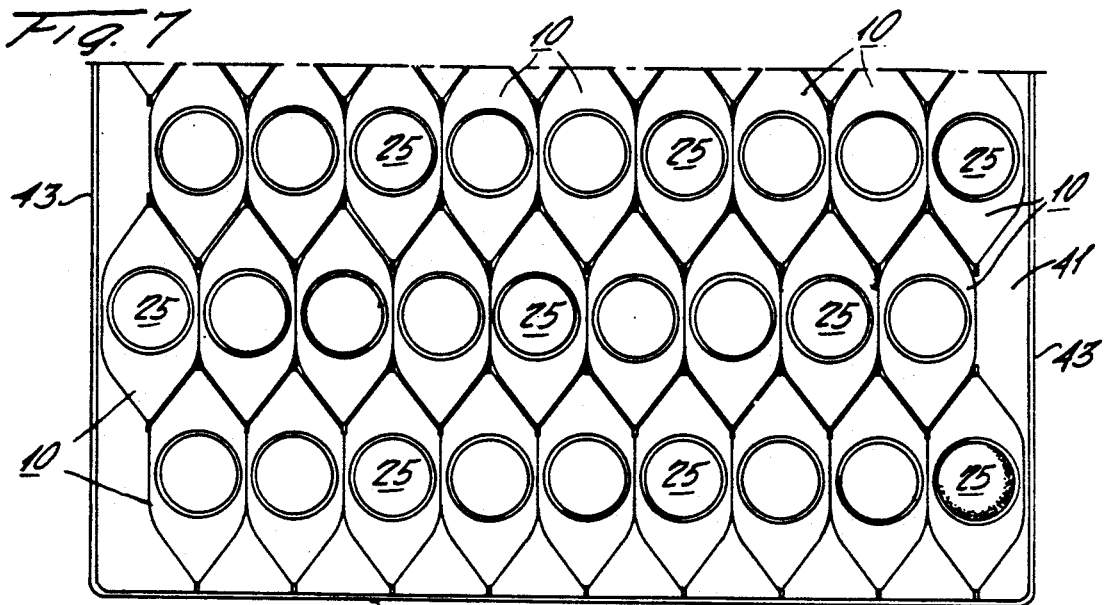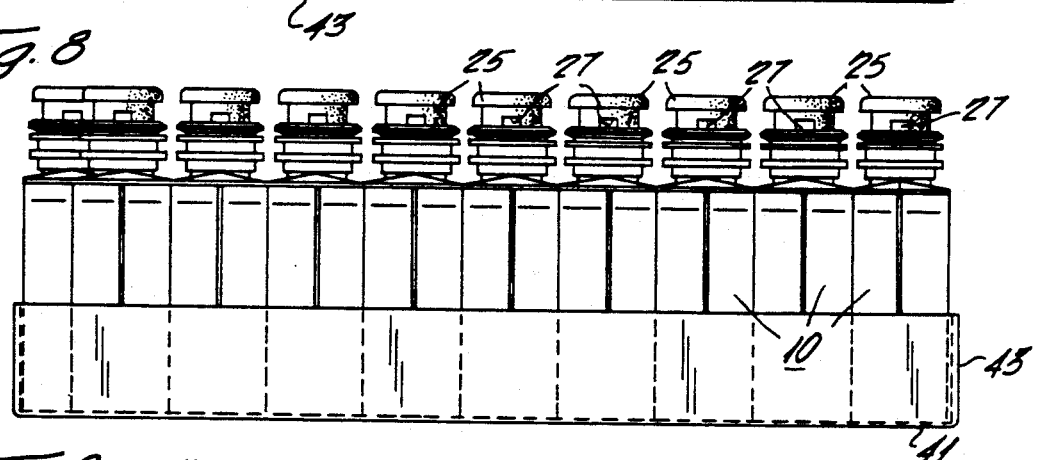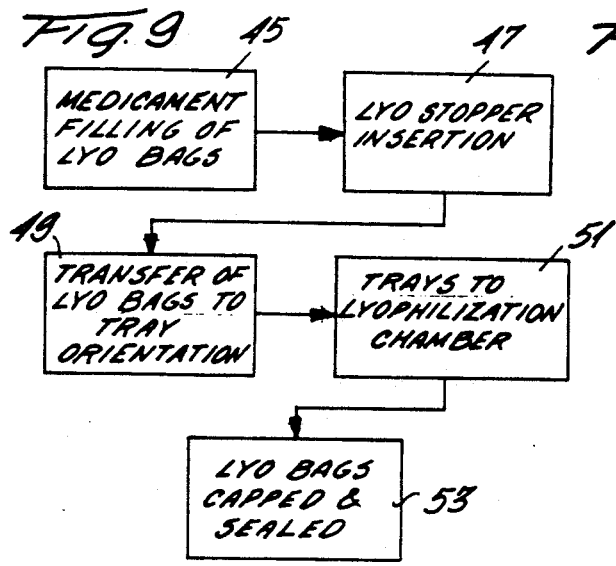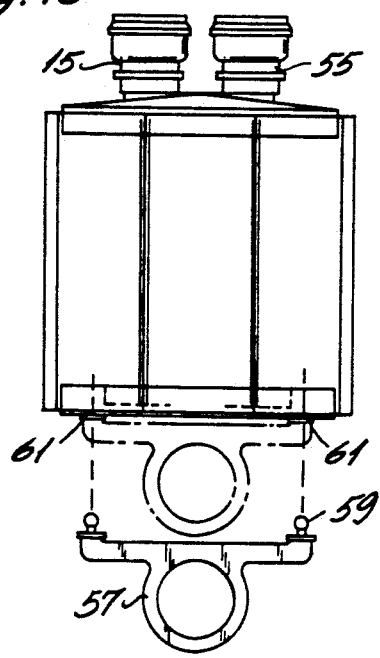

LYOPHILIZATION DEVICE

FIELD OF THE INVENTION

The present invention relates to a lyophilization device and more particularly to a container of this type used in the process of freeze drying pharmaceutical products to increase the storage life of the medicine. The present invention may also be used to dispense the medicine after it has been reconstituted.

BACKGROUND OF THE INVENTION

Lyophilization is a process which has become more common in the pharmaceutical industry in present times as the need to increase the storage life of pharmaceutical products increases. In the past, with relatively inexpensive drugs, or with drugs which are in tablet or capsule form, the shelf life or storage life has not been a significant factor. However, as drugs become more complex and specialized, the need for longer storage life has increased.

Lyophilization is of particular value when the pharmaceutical product is particularly sensitive to solvents such as water. During lyophilization, the product in liquid form is cooled until it is completely frozen, typically to temperatures at or below minus 50° C. Once the product has been completely frozen, the water or other solvent will separate from the solute ingredients. It is then possible to remove the separated water or other solvent from the frozen product by heating the contents slowly, under carefully controlled conditions, and under high vacuum so that the solvent leaves the products through sublimation.

If too much heat is added too quickly, the product will melt. If the rate of sublimation is too slow, the manufacturing cost will make the process unacceptable. It is not desirable to tie up expensive equipment and staff, nor is it desirable to subject the ingredient to an extremely long sublimation cycle. Clearly, optimization for each product and solvent will depend upon the particular ingredients but it is always a goal.

There are two stages in the lyophilization cycle. First, the product must be frozen. It is not generally possible to accurately divide a large quantity of freeze dried product into individual dosages and place those individual doses in separate containers. Rather, the aqueous solution is accurately measured into separate containers and these containers are then placed in the lyophilization apparatus.

Typically, a number of containers are placed on a metal tray, so that heat transfer can be optimized, and then the tray is placed in the lyophilization chamber. Temperature is then reduced until the product and solvent freeze.

The second phase in the lyophilization cycle is the drying process. Drying is accomplished by a mixture of heat transfer and mass transfer at the same time. The drying process is conducted under vacuum so that the vapor pressure of water or other fluids is relatively low. Heat is applied to transform ice crystals into water vapor. This vapor migrates through the rest of the product and escapes out the vacuum vent at the top of the container. Clearly, if a very long period of time is taken, there is plenty of opportunity for the water vapor to escape from the entire dried product. In addition, this is clearly inefficient. If heat energy is applied at too high of a rate, water vapor is produced faster than it can be removed from the dried product. As a result, the product may re-solubalize or may be insufficiently dried because the passageways for the water vapor are closed off.

In a properly run lyophilization process, the shelf temperature, vacuum level, heat transfer, and other variables are optimized and an acceptable, saleable product is produced. Once the proper lyophilization is completed, the stopper is then fully inserted into the container, thereby preserving the integrity of the product. Aluminum or plastic seals and other means for ensuring product integrity are employed to make the container ready for the market place. While the process itself is quite satisfactory, it would be a great advantage in the art if the process could be done faster. Ideally, even though the particular process is optimized, complete lyophilization may take many hours to be completed. It would be highly desirable if this time could be reduced significantly without running any risk of adversely affecting the product in its final form.

Presently, a great number of containers are manufactured for use in the lyophilization process, wherein a liquid is placed in a vial type container, partially stoppered to permit escape of the water vapor during the sublimation step, followed by complete stoppering through the application of force along the axis of the container.

Glass containers have historically been used as pharmaceutical lyophilization containers because glass has the desired clarity, resistance to chemical attack and physical stability. One principal drawback of glass as a container for pharmaceutical products is that the glass containers are not directly usable for intravenous or IV administration to a patient without venting.

Because the glass walls are rigid and do not collapse as the liquid is withdrawn, it is necessary to provide an additional venting mechanism in order to use the same container for storage and administration to the patient. Particularly when hazardous or highly sensitive medicaments are employed, it is not desirable to reconstitute the freeze dried medicine in a glass vial and transfer it to a more flexible plastic container for use in intravenous administration.

Glass containers also have the drawback of potential breakage. If breakage occurs during the lyophilization process in the chamber, glass particles could possibly enter the unstoppered product container, rendering a product that could be dangerous to use in humans.

In some instances, drugs used for treatment of cancer and other diseases are themselves very dangerous. For these toxic, irritating or limited-exposure drugs, breakage of glass containers is considered a serious threat to the health of hospital personnel who work with those drugs on a daily basis.

Nonetheless, while there are many drawbacks to the use of glass in lyophilization processes, to this date, an effective and total solution to all of the problems using non glass containers has not been discovered.

Clarke et al, U.S. Pat. No. 4,415,085, proposes a dry system using flexible bags of two layers of plastics. This system does propose certain advantages of plastic containers over those made from glass. Primarily, the rigidity of glass containers and the need to vent them are listed as two of the major drawbacks. The flexible package of the Clarke et al design is formed from a plastic film laminate having a polyethylene terephthalate film bonded to a medium density polyethylene film. It is clear from reading the Clarke et al patent that an entirely new system would be needed to modify this container for use in a lyophilization processing facility which had previously been designed for glass vials.

Another flexible container which is apparently quite suitable for sterilized medical situations in which blood bags or IV bags are used is shown in Mahal, U.S. Pat. No. 4,479,989. Mahal described the advantages of linear low density polyethylene and other materials suitable for IV bags.

Plastic medical solution containers present different problems for port construction. Two patents which describe port and closure constructions are McPhee, U.S. Pat. Nos. 4,484,916, and 4,592,092. Two other medical storage bags, more suitable for use as blood bags, are described in Herbert, U.S. Pat. Nos. 4,516,977 and 4,561,110. Both of these later patents describe multiple layer bags for medical purposes, in which one of the layers is a polyethylene film.

In summary, while a number of plastic containers have been proposed for use in intravenous administration of medical products, none of these plastic containers appear to be useful as a substitute for the glass vials in conventional lyophilization processes. It is, therefore, an object of this invention to produce such a container. Yet another object of this invention is to provide a flexible container for use in the lyophilization process which is superior to glass as an IV container.

Other objects will appear hereinafter.

SUMMARY OF THE INVENTION

It has now been discovered that the above and other objects of the present invention may be accomplished in the following manner. Specifically, it has been discovered that an improved lyophilization container may be manufactured from flexible synthetic materials. This device is admirably suited for use in conventional glass vial lyophilization equipment, and possesses all of the advantages of glass and none of the disadvantages. Specifically, there is sufficient structural integrity to permit use of the stoppering method used presently on glass vials only. In addition, the efficiency of the process is increased, wherein at least two times as many individual containers can be completely processed through the freezing and drying cycle as could previously be accomplished using glass containers or vials.

In one embodiment, the lyophilization device of the present invention includes a top end having at least one lyophilization port axially extending upward. This port permits the use of a lyophilization stopper which is partially seated during the freezing/drying cycle and which is fully seated by a downward pressure at the end of the cycle. The end defines a non round shape which may be generally polygonal, preferably oval so that the cross section is longer than it is wide, and is somewhat diamond shaped. The shape is polygonal, such as four or six sided, with not quite squared off junctions between the sides, more oval than sharply defined. Other shapes such as square and diamond shapes may also be used.

Also included is a bottom end which generally has the same perimeter shape as the top. The optimum shape will be selected depending upon molding efficiencies, the flexibility of the wall portion between the two ends, and the size of the lyophilization shelf being used. It is understood that these polygonally sided containers will increase the number of individual devices which can be nested in a given tray, thereby increasing the efficiency of the processing equipment. Square shapes give the maximum number of containers per tray, but other factors are also considered, such as use of the containers for IV treatment once the contents have been reconstructed.

One advantage of the present invention is that containers of the present invention, having large adjacent, abutting side walls, will confront and engage one another in the lyophilization tray in a honeycomb effect. In this embodiment, column strength is derived from nesting which exceeds that strength offered by individual containers.

As was stated above, the bottom end has the same general shape as the top. The bottom end preferably has a substantially flat bottom so that the device will have maximum contact with the tray on which it is placed for better heat transfer. In a preferred embodiment, the bottom end further includes means for attaching an IV hook. This attachment means should not in any way detract from the flatness of the bottom end.

In between the top and bottom end caps is a wall portion which may be attached to both with a heat or adhesive type seal and which completes the container device. The inside surface of the wall portion is preferably drug compatible and the wall contains sufficient buckle strength to withstand the vertical force necessary for fully seating the stopper which is to be fitted into the lyophilization port. The wall portion is flexible and pliable in that it is sufficiently supple to bend freely and repeatably without breaking, creasing or cracking.

In another embodiment, the entire container can be made as a one-piece, blow molded container, where the top, bottom and walls are formed in one integral process. In this embodiment, the preferred material is a polyolefin such as polyethylene, although any moldable, drug compatible material may be used. There are also some techniques where multilaminar blow-molding can produce a container with flexible, pliable walls according to the present invention.

A preferred material from which the wall portion is made is a multilaminar film in which the inner layer is drug compatible and the outer layer contributes substantially to the buckle strength or column strength of the bag. This material may include middle layers in order to increase puncture resistance, heat transfer, moisture vapor barrier or other properties. In a most preferred embodiment, the inner layers are formed from polyolefins such as polyethylene, and the outer layer is formed from polyethylene terephthalate.

It has also been found desirable to manufacture the end caps from polyolefins such as polyethylene. All of these materials have been found to be admirably compatible with pharmaceutical products, whether in a freeze dried condition or in solution. If the device of this invention is one piece, it will probably be fabricated from a single material, although multiple layer molding techniques can also be used. The same criteria are used in the selection of the proper material. Any non glass material may be considered for use as a material for the container.

Also contemplated as part of the present invention is a method providing a plurality of containers having lyophilization product therein. The method includes the use of the novel lyophilization device of this invention on trays such as are used with glass vials, resulting in important improvement in processing time.

Finally, the present invention allows for increased efficiencies and reduced rejects when a preferred stopper and port finish combination is employed. Specifically, the stopper and port include means to lock the stopper in a first position for lyophilization and a second position for subsequent use. One preferred locking means is a locking ring on either the stopper or the inside finish of the port, and a pair of grooves on the other component, where the grooves define the first and second positions.

BRIEF DESCRIPTION OF THE DRAWINGS

These and other objects of the present invention and the various features and details of the operation and construction thereof are hereinafter more fully set forth with reference to the accompanying drawings, where:

FIG. 1 is a side elevational view of a preferred lyophilization container, having semi-rigid or flexible, thin, transparent or translucent, pliant sidewalls, upper and lower ends, and a cylindrical neck portion whose terminal open end is sealed by means of a lyophilization stopper and an outer closure member.

FIG. 2 is a plan view of the lyophilization device shown in FIG. 1, illustrating its generally polygonal cross section.

FIG. 3 is a bottom plan view of the lyophilization device shown in FIG. 1, again showing its polygonal, six sided, generally oval shape and its flat, planar bottom.

FIG. 4 is pictorial view of the rigid synthetic upper and lower cap members, showing the polygonal oval shaped top end and bottom end.

FIG. 5 is an enlarged sectional elevational view taken along lines 5, 5 of FIG. 1, showing certain details of construction.

FIG. 6 is a greatly enlarged view of the details contained within the dot and dash circle of FIG. 5 and designated FIG. 6, showing schematically the laminated synthetic construction of one embodiment of the side wall of the device shown in FIGS. 1 and 5.

FIG. 7 is a plan view illustrating intermeshing, high density lyophilization tray nesting, achieved with the lyophilization container shown in FIGS. 1 through 6.

FIG. 8 is a front elevational view of FIG. 7 showing additional details of the tray stacking of the lyophilization devices which at this point in the process contain liquid medicament and have lyophilization stoppers inserted in the necks of the containers in a partially seated position, all prior to being placed in the lyophilization chamber.

FIG. 9 is a block diagram illustrating a sequence of events which the semi-rigid lyophilization devices of the present invention will undergo in a production run.

FIG. 10 is a side elevational view of a modified lyophilization device, similar in all respects to the lyophilization devices shown in FIGS. 1 through 8, but having a detachable hanger member shown in full lines in the drawing, prior to being attached to the flat co-planer bottom of the lyophilization bag as shown in the dot and dash line. The upper terminal end is modified to include two necks both stoppered and overcapped with a closure member.

FIG. 12 shows the stopper in a partially seated position and FIG. 13 shows the fully seated position.

DETAILED DESCRIPTION OF THE PREFERRED EMBODIMENT

Figure 11:
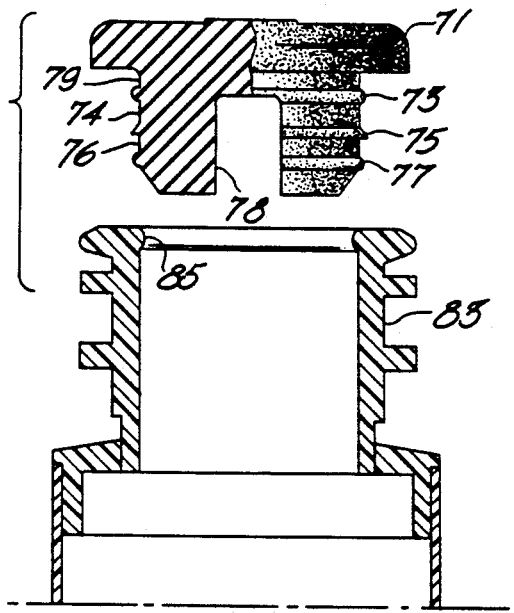
FIGS. 11, 12, and 13 are enlarged sectional elevational views showing the preferred stopper and finish of the present invention, where

As shown in FIG. 1, generally by the reference numeral 10, a lyophilization device includes a top end 11 and bottom end 13 which are non round, and generally polygonal and/or oval in shape. The top end 11 includes a lyophilization port 15. Heat sealed to both the top 11 and the bottom 13 is a wall portion 17 which is made from a semi-rigid or flexible, thin, transparent or translucent, pliable material. Any non glass material may be considered. The wall portion 17 assumes the same cross section as the end 11 and 13 and the entire device is admirably suited for use in a lyophilization process to freeze dry liquid containing medicaments. It is to be noted that one preferred shape is shown in these drawings. Other shapes, from square to very elongated ovals can also function effectively.

The top end 11 and lyophilization port 15 contain an opening 19 which is sized for conventional lyophilization stoppers. The ends 11 and 13 are preferably made from polyolefin resins such as polyethylene or polypropylene, because this material has a proven compatability record with pharmaceutical products. Polyethylene is cost effective and is suitable for injection molding and heat sealing without any significant difficulty.

Separating the ends 11 and 13 and forming the container, is a wall portion 17 which is to be manufactured from a flexible, pliable material, preferably which has an inside surface that is drug compatible. Certain types of polyethylene and other polyolefins are very inert, low extractable materials which are drug compatible and can be selected for use, at least for the inside of the wall portion 17. It has been found that a wall portion 17 which is between 5 and 20 mils thick will be flexible and pliable, and will function adequately in the practice of this invention.

In a preferred embodiment, the wall portion 17 will be sufficiently thick and have buckle resistance or column strength so that when the lyophilization stopper is completely inserted in the opening 19 of port 15, the wall portion 17 will resist the force used to seat the stopper.

As previously noted, nesting of the containers to obtain a honeycomb effect will increase column strength because of the unique features of the present invention. The polygonal shape permits large, adjacent abutting side walls to confront and engage one another to give the added support.

As shown in FIGS. 3 and 4, the bottom 21 of the bottom end 13 is flat. One of the preferred embodiments of the present invention is the inclusion of a flat bottom, so that improved heat transfer can take place. Specifically, it is a preferred embodiment that the flat bottom 21 have a flatness sufficient to cause 10% to 50% of the bottom 21 to be in contact with the shelf. Conventional glass vials have about 0.1% in contact.

Typically, glass vials have a rounded concave bottom which presents a blanket of air, insulating the contents from the tray upon which it is placed. Prior art glass vials will trap or enclose up to 10 times as much air volume as is trapped by containers of the present invention. This represents a major improvement in thermal resistance.

Glass vials are not yet commonly fabricated with extreme bottom flatness without simultaneously increasing built-in stress so that the glass shatters at low process temperature. Thus, as little as one tenth as much surface contact is made with the glass vial, in theory at least, than is made with the flat bottom 21 of the present invention. The thermal conductivity of polyolenfin resins is superior to glass as well. Therefore, in a preferred embodiment, increased conductivity of a factor of 5 or more and increased surface area of a factor of up to 10 or more provides for a tremendous increase in thermal conductivity. Not only can the liquid contents be frozen faster due to increased thermal conductivity, but the rate of drying can be controlled much more precisely for further optimization of the process conditions.

Also shown in FIG. 3 are posts 18, which are mounted or molded near the ends 17a of wall 17, for additional column strength if needed. Also, wall 17 can be formed from flexible, pliable tubing, which would eliminate heat seal seams at the ends 17a of wall portion 17.

As noted above, the wall portion 17 is preferably clear or translucent so that the freeze dried medicament 23 can be seen. This ensures that when the medicament 23 is reconstituted, such as by the addition of diluent, quick visual inspection will verify that all of the medicament has been reconstituted into solution, and the solution can be evaluated for unwanted turbidity or haze.

As shown in FIG. 5, the stopper 25 fits inside the port opening 19 of lyophilization port 15. The stopper 25 has a central core discontinuity 27 which serves as a vent during the lyophilization process. Specifically, when the stopper 25 is partially inserted into the opening 19 of port 15, the central core discontinuity 27 extends above the top portion 15a of lyophilization port 15.

Once the medicament has been freeze dried, the stopper is then fully inserted into the port opening 19 of lyophilization port 15. An outer closure member 29 is then added to secure the stopper. This closure 29 is shown as having an easily removable top portion to permit easy access to the stopper 25.

The entire top end 11 including the lyophilization port 15 is bonded to the wall portion 17 at junction 31. Similarly, the bottom end 13 is sealed to the wall portion 17 at junction 33. Note in FIG. 5 that the bottom 21 of the bottom end 13 is substantially flat and provides the advantages described above. Polyethylene terephthalate is particularly suitable for forming visually acceptable heat melt junctions. Other materials may be used when adhesive junctions are employed.

As shown in the enlarged portion of FIG. 6, the wall portion 17 may be manufactured from a laminated or coextruded film in order to achieve a plurality of properties. The inner layer 35 is preferably made from a very inert, low extractable, flexible, pliable drug compatible material such as certain polyethylenes or other polyolefins. This layer would be approximately 6 mils thick and would comprise the layer which is in contact with the drug, both in solution and after freeze drying. On the exterior of the wall portion 17 a layer 37 is provided to give increased buckle strength. This layer 37 is preferably manufactured from polyethylene terephthalate. This material provides increased buckle strength or column strength and helps provide a more attractive bond, in one embodiment because it does not melt when the inner layer 35 is melted if junctions 31 and 33 are heat melt junctions. The use of an outer layer 37, made from a material such as polyethylene terephthalate also permits an overall thinner wall portion 17.

In a preferred embodiment, a middle or center layer 39 is provided, which can for example, provide tear and puncture resistance and an effective moisture vapor barrier. Linear low density polyethylene is a preferred material in this case. A 2 mil thick layer 39 will give an overall thickness of about 10 mils.

Although many other non glass materials are useful in the present invention, polyethylene brings particularly good properties to the present invention. Specifically, some materials do not have a low glass transition temperature at which the polymer changes from a rubbery state to a brittle state. Nylon, for example, has a glass transition temperature of about $-50°$ C. and may therefore be brittle at extremely low temperatures. It is not uncommon to reach temperatures of minus 50° C. when freezing and drying medicaments in pharmaceutical lyophilization chambers. Polyethylene, on the other hand, has a glass transition temperature of $-120°$ to $-125°$ C., thereby insuring good toughness properties at operating temperatures. Polypropylene, by way of contrast, has a glass transition temperature of $-18°$ to $-200°$ C. and polycarbonates have a glass transition temperature of $\pm 150°$ C.

While polyethylene terephthalate, low density polyethylene and medium density polyethylene have been combined into films prior to the present invention, they have not been constructed as described herein. For example, Boyd et al, U.S. Pat. No. 4,533,578 described a 3-ply trash bag in which linear low density polyethylene and polyethylene terephthalate are employed in combination. Trash bags, are, of course, different than wall portions of lyophilization containers and the problems encountered by U.S. Pat. No. 4,533,578 are not related to those encountered herein.

An alternative embodiment would be to blow mold a lyophilization container according to the present invention, forming the device as one piece. If the molting material is drug compatible, and an appropriate bottom flatness can be achieved, this alternative may permit less expensive containers to be produced in high volume.

It is also within the scope of this invention to construct the containers of this invention from other materials. Non-glass materials which can be formed into the device of this invention include various natural and synthetic elastomers, perhaps with structural support included internally in the form of ribs and the like. In selecting the material, it is preferred that the wall portion 17 be flexible and pliable, as previously described.

As shown in FIG. 7, a plurality of containers 10 have been assembled on the surface 41 of a tray which is used for placing lyophilization devices in the apparatus used for that purpose. As is noted, the generally polygonal shaped cross section allows for optimization of nesting of the many units. Other shapes are possible with longer and thinner shapes or wider and thicker shapes as desired by the end user. It is also noted that the sides are not quite as squared off as shown in FIG. 4, due to the formation of the junctions and the continuity of the wall portions 17. In this arrangement, the various walls 17 define large planar side walls which are adapted to confront and engage adjacent walls 17, to achieve a honeycomb effect.

In a typical 48 inch by 60 inch shelf, 660 round bottles can be placed. When the generally polygonal cross section of the present invention is employed, this number increases to up to 1100 or more containers on the same 48 inch by 60 inch shelf. The efficiencies of this design becomes clear when it is realized that nearly 67% more containers can be placed on the same tray. When this efficiency is compounded with the increased surface area due to the preferable flat surface 21 of the bottom cap 13 as previously described, it is clear that much greater efficiency and economy can be achieved according to the present invention.

When the tray is loaded as shown in FIGS. 7 & 8, it is then placed in the lyophilization chamber. The stopper 25 extends into the lyophilization port 15 only part way, so that the discontinuity 27 remains exposed to the outside. Thus, when the vacuum is placed on the chamber, the water or other fluids which are escaping by sublimation can exit the chamber through this discontinuity 27.

The overall process of the present invention as shown in FIG. 9 includes employment of the design shown in FIGS. 1 through 8. These containers are filled with the appropriate quantity of medicament in liquid form and the stopper 25 is inserted to the degree shown in FIG. 8. This takes place in stages 45 and 47. Then the containers are transferred to an appropriate tray orientation at stage 49, such as shown in FIGS. 7 & 8 and the trays are placed on a shelf in a lyophilization chamber 51. At this point in time, the temperature is rapidly decreased, and, because the tray bottom 41 and sides 43 are manufactured from metal, the bottoms 41 and sides 43 provide the principal heat transfer heat mechanism.

Some lyophilization chambers use trays which include a slide-out bottom, which allows the contents of the tray to rest directly on the chamber shelf. This tray embodiment is admirably suited to the present invention because the flat bottom of the containers of this invention permits maximum heat transfer.

Because of the increased surface area of the flat bottom 21 as shown above, the contents reach a freezing temperature more quickly. Next, the chamber is slightly warmed and a vacuum is drawn so that the sublimation and desorption processes take place. The medicament is left behind as the water or other solvent is removed, resulting in a finished product that is stable and free from chemical or biological degradation. It is ready to be reconstituted at the time of intended use.

The trays are subjected to a capping and sealing step in box 53. This step comprises the application of force on the stopper 25, so that the stopper 25 is fully sealing the lyophilization port 15. A conventional seal 29 is added using capping machines currently available. The port 15 shown in FIG. 5, for example, includes a handling ring 15a which is used as a support ring during the final capping process, thereby eliminating the need to have the container walls support the much greater closure sealing loads sometimes encountered in automative assembly. These loads are generally higher than the load or force required to seat the stopper at the end of the lyophilization cycle.

In stoppers of 28 millimeters or larger, it is practical to add diluent to reconstitute the freeze dried products using a needle at a location sufficiently spaced from the stopper axis and close to the periphery, to leave room for the larger administration spike. Because of the flexible, pliable walls, especially for thinner, elongated embodiments of the invention, it is often possible to allow gravity drainage of the reconstituted material. However, when it is desirable to vent the container, an administration spike containing a vent device can be used. In stoppers smaller than 28 mm, it may be necessary to use the second port 55 shown in FIG. 10 for adding the reconstituting fluid.

A hanging hook 57 can be inserted using snap ball 59 and hole 61 in base 21 of the bottom end cap 13. Since different medicaments and different manufacturers can be distinguished by having different hanger hooks 57, this feature can be added later in the manufacturing process to give distinctiveness to the products and to avoid confusion when the product is ultimately used.

Figure 12:
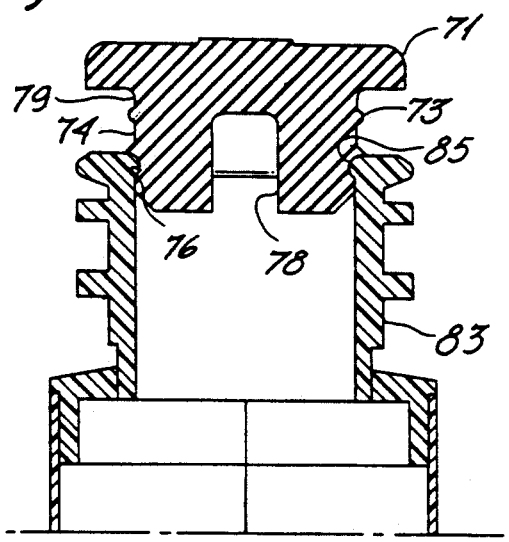
Figure 13:
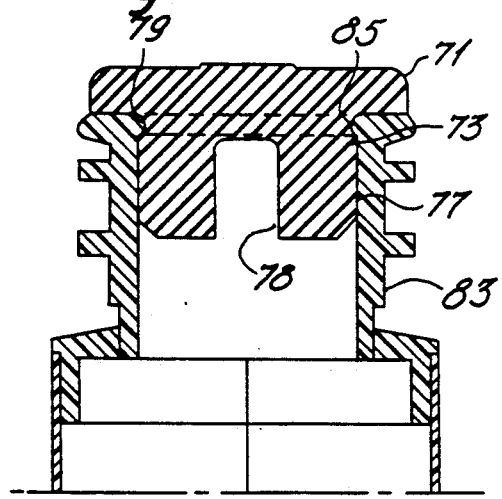

As shown in FIG. 11-13, an improved stopper and port finish has been found to be highly suited for use with the lyophilization device of this invention. In FIG. 11, a port 83 is shown, which is similar to port 15 as previously described with respect to FIGS. 1-5 for example. Port 83 also includes an inwardly disposed annular ring 85 which is centered about the axis of the port 83.

The stopper 71 is provided with outwardly extending annular rings 73, 75 and 77. These rings 73, 75 and 77, together with the stopper top 71, define grooves 74 and 76, and also groove 79. When the stopper 71 is first inserted into port 85, as shown in FIG. 12, the ring 85 fits into groove 76, thereby positioning the stopper 71 in the correct position for the lyophilization process described above. The central core discontinuity 78 is above the top ring 85 and the lyophilization process can be accomplished as described and schematically shown in FIG. 9, box 51.

Once the lyophilization process has been completed, the stoppers 71 are fully inserted into the port 83. In many lyophilization chambers, the space between shelves is decreased systematically in an accordion like manner. All of the stoppers are completely seated in the containers by the downward force of the shelf above them. Because the container walls have sufficient buckle strength to withstand the vertical force during end of the cycle seating, the stopper 71 will move to a fully seated position shown in FIG. 13. The stopper 71 locks into port 83 to form a complete seal of the container as annular ring 85 engages groove 79, thereby insuring that the stopper will not rise up from the fully inserted position and compromise the integrity of the product once the container leaves the lyophilization chamber.

As shown in FIGS. 11-13, the stopper has three annular rings 73, 75 and 77, defining grooves 74 and 76 as well as groove 79 adjacent the top of stopper 71. Groove 76 is located to hold stopper 71 in an effective location during the lyophilization process, and groove 79 helps to hold the stopper in its fully seated position. Groove 74 has no direct function, but is formed because there may need to be spacing between groove 74 and groove 79 for optimum processing. Clearly, in some designs where ring 85 can interengage grooves 74 and 79 using a common ring so that ring 75 is not needed, that ring 75 can be eliminated. It is important to note that none of the rings 73,75 or 77, grooves 74 and 76 need to be continuous. Partial grooves or rings, or bump like projections are common in the stopper industry and use of partial grooves or rings is part of this invention.

What is claimed is:

1. A lyophilization device, for a stopper comprising:
    a top end having at least one lyophilization port axially extending upward, said top end defining a non-round shape;
    a bottom end having generally the same shape as said top; and
    a non-glass wall portion between said top and bottom ends defining a container, said wall portion having an inside surface which is drug compatible and having a predetermined buckle strength to withstand vertical force during insertion of a stopper, said non-round shape being oval.

2. The device of claim 1 where said bottom end includes a substantially flat bottom.

3. The device of claim 1 wherein said wall portion is formed from a multilaminar film in which the inner layer is drug compatible and the outer layer contributes substantially to the buckle strength.

4. The device of claim 3 wherein said inner layer and ends are formed form polyolefin.

5. The device of claim 1 wherein said bottom end includes means for attaching an IV hook.

6. The device of claim 1 which further includes a lyophilization stopper.

7. The device of claim 6 wherein said stopper and said port include cooperative means for positioning said stopper in a first position for lyophilization and a second position for seating said stopper.

8. A lyophilization device, for a stopper comprising:
a top end having at least one lyophilization port axially extending upward, said top end defining a non-round shape;
a bottom end having generally the same shape as said top end; and
a wall portion between said top and bottom ends defining a container, said wall portion formed from a multilaminar film wherein the inner layer is drug compatible and the outer layer contributes substantially to the buckle strength and is formed from polyethylene teraphthalate.

9. A lyophilization device, for a stopper comprising:
a top end having at least one lyophilization port axially extending upward, said top end defining a non-round shape;
a bottom end having generally the same shape as said top end; and
a wall portion between said top and bottom ends defining a container, said wall portion being formed from a multi-laminar film wherein the inner layer is drug compatible, the outer layer contributes substantially to the buckle strength, and the middle layer having an increased punctured resistance made of a linear low density polyethylene.

10. A lyophilization device, for a stopper comprising:
a top end having at least one lyophilization port axially extending upward, said top end defining a non-round shape;
a bottom end having generally the same shape as said top end;
a non-glass wall portion between said top and bottom ends defining a container, said wall portion having an inside surface which is drug compatible and having a predetermined buckle strength to withstand vertical force during stopper insertion; and
a lyophilization stopper;
said port and stopper including cooperative means for positioning said stopper in a first position for lyophilization and a second position for sealing said port comprising a partial or continuous annular ring and groove assembly aligned to define the first and second positions.

11. A lyophilization device, for a stopper comprising:
a top end having at least one lyophilization port axially extending upward, said top end having a predetermined cross sectional shape;
a bottom end having generally the same cross sectional shape as said top end, and having a substantially flat bottom; and
a flexible, pliable wall portion between said top and bottom ends to define a container, said wall portion having an inside surface which is drug compatible and a predetermined buckle strength to withstand vertical force during stopper seating;
said wall portion being multilaminar, wherein at least the inner layer is drug compatible and the outer layer contributes substantially to the buckle strength; and
said shape being polygonal including three sets of generally parallel sides.

12. A lyophilization device, for a stopper comprising:
a top end having at least one lyophilization port axially extending upward, said top end having a predetermined cross sectional shape;
a bottom end having generally the same cross sectional shape as said top end, and having a substantially flat bottom; and
a flexible, pliable wall portion between said top and bottom ends to define a container, said wall portion having an inside surface which is drug compatible and a predetermined buckle strength to withstand vertical force during stopper seating of a stopper;
said wall portion being multilaminar, wherein at least the inner layer is drug compatible and the outer layer contributes substantially to the buckle strength; and
at least said inner layer and said ends being formed from polyolefin and said outer layer being formed from polyethylene teraphthalate.

13. The device of claim 12 wherein said bottom end includes means for attaching an IV hook.

14. The device of claim 12 which further includes a lyophilization stopper.

15. The device of claim 14 wherein said stopper and said port include cooperating means for positioning said stopper in a first position for lyophilization and a second position for sealing said port.

16. The device of claim 12 wherein said top and bottom ends and said wall portion are molded together in a one step process.

17. A lyophilization device, for a stopper comprising:
a top end having at least one lyophilization port axially extending upward, said top end having a predetermined cross sectional shape;
a bottom end having generally the same cross sectional shape as said top end, and having a substantially flat bottom; and
a flexible, pliable wall portion between said top and bottom ends to define a container, said wall portion having an inside surface which is drug compatible and a predetermined buckle strength to withstand vertical force during stopper seating of a stopper;
said wall portion being multilaminar, wherein at least the inner layer is drug compatible and the outer layer contributes substantially to the buckle strength; and
a lyophilization stopper; and
said port including cooperating means for positioning said stopper and a first position for lyophilization and a second position for sealing said port comprising a partial or continuous annular ring and groove assembly aligned to define first and second positions.

18. A lyophilization container comprising:
a top member having a lyophilization port for mounting a sealing closure;
a bottom member;

an elongated body member between the top and bottom members, at least said body member being made of a flexible, pliable material and said members being of a predetermined configuration whereby the container has a predetermined buckle strength to withstand a vertical sealing force seating a stopper in said port and sufficient flexibility to allow gravity drainage of contents; and said body portion being formed from a multilaminar film wherein the inner layer is a polyethyelene and the outer layer is polyethylene teraphthalate.

19. The device of claim 18 wherein said body member defines large planar side walls adapted to confront and engage adjacent sidewalls when a plurality of said devices are placed proximate one another.

20. The device of claim 18 which further includes a lyophilization stopper.

21. The device of claim 20 wherein said stopper and said port include cooperating means for positioning said stopper in a first position for lyophilization and a second position for sealing said port.

22. A lyophilization container comprising:
a top member having a lyophilization port for mounting a sealing closure;
a bottom member;
an elongated body member between the top and bottom members, at least said body member being made of a flexible, pliable material and said members being of a predetermined configuration whereby the container has a predetermined buckle strength to withstand a vertical sealing force seating a stopper in said port and sufficient flexibility to allow gravity drainage of contents; and
a lyophilization stopper, said port and stopper including cooperating means for positioning said stopper in a first position for lyophilization and a second position for sealing said port including a partial or continuous annular ring and groove assembly aligned to define said first and second positions.

23. A lyophilization device, for a stopper comprising:
a top end defining a non-round shape and having at least one lyophilization port for a stopper;
a bottom end having generally the same shape as said top end; and
a non-glass wall portion between said top and bottom ends defining a container, said wall portion having an inside surface which is drug compatible and having a predetermined buckle strength to withstand vertical force during stopper insertion, the cross sectional shape of said device being generally arcuate.

24. A lyophilization device for a stopper, comprising:
a top end having at least one lyophilization port defining a non-round cross section;
a bottom end having generally the same cross section as said top; and
a non-glass wall portion between said top and bottom ends defining a container, said wall portion having an inside surface which is drug compatible and having a predetermined buckle strength to withstand vertical force during insertion of a stopper, said non-round shape being polygonal including three sets of generally parallel sides.

25. A lyophilization device, comprising:
a top end having at least one lyophilization port axially extending upwardly, said top end defining a non-round shape;
a bottom end having generally the same shape as said top end; and
a non-glass wall portion between said top and bottom ends defining a container, said wall potion having an inside surface which is drug compatible and having a predetermined buckle strength to withstand vertical force during insertion of a stopper, said non-round shape being oval and including three sets of generally parallel sides.

26. A lyophilization device, comprising:
a top end having at least one lypohilization port axially extending upwardly, said top end defining a non-round shape;
a bottom end having generally the same shape as said top end; and
a non-glass wall portion between said top and bottom ends defining a container, said wall portion having an inside surface which is drug compatible and having a predetermined buckle strength to withstand vertical force during insertion of a stopper, said non-round shape being oval, said wall portion defining large planar side walls adapted to confront and engage adjacent side walls when a plurality of said devices are placed proximate one another.

27. A lyophilization device, comprising:
a top end having at least one lyophilization port axially extending upwardly, said top end defining a non-round shape and formed of polyethylene;
a bottom end having generally the same shape as said to end and formed of polyethylene; and
a non-glass wall potion between said top and bottom ends defining a container, said wall portion having an inside surface which is drug compatible and having a predetermined buckle strength to withstand vertical force during insertion of a stopper, said non-round shape being oval, said wall portion being formed from a multilaminar film including a drug compatible inner layer formed of polyethylene and an outer layer contributing substantially to the buckle strength.

28. A lyophilization device, comprising:
a top end having at least one lyophilization port axially extending upwardly, said top end defining a non-round shape;
a bottom end having generally the same shape as said top end; and
a non-glass wall portion between said top and bottom ends defining a container, said wall portion having an inside surface which is drug compatible and having a predetermined buckle strength to withstand vertical force during insertion of a stopper, said non-round shape being oval, said wall portion defining large planar side walls adapted to confront and engage adjacent side walls when a plurality of said devices are place proximate one another.

29. A lyophilization device, comprising:
a top end having at least one lyophilization port;
a bottom end; and
a non-glass wall portion between said top and bottom ends defining a container of a generally oval shape, said wall portion having an inside surface, which is drug compatible, and said wall portion having a predetermined buckle strength to withstand vertical force during insertion of a stopper.

30. The device of claim 29 wherein said shape includes three sets of generally parallel sides.

31. The device of claim 29 where said bottom end includes a substantially flat bottom.

32. The device of claim 29 wherein said wall portion defines large planar side walls adapted to confront and engage adjacent side walls when a plurality of said devices are placed proximate one another.

33. The device of claim 29 wherein said wall portion is formed from a multilaminar film in which the inner layer is drug compatible and the outer layer contributes substantially to the buckle strength.

34. The device of claim 33 including a middle layer having an increased puncture resistance.

35. The device of claim 34 wherein said middle layer is linear low density polyethylene.

36. The device of claim 33 wherein said inner layer and ends are formed from polyolefin.

37. The device of claim 36 wherein said inner layer and ends are formed from polyethylene.

38. The device of claim 33 wherein said outer layer is formed from polyethylene.

39. The device of claim 29 wherein said bottom end includes means for attaching an IV hook.

40. The device of claim 29 which further includes a lyophilization stopper.

41. The device of claim 40 wherein said stopper and said port include cooperative means for positioning said stopper in a first position for lyophilization and a second position for seating said port.

42. The device of claim 41 wherein said cooperating means includes a partial or continuous annular ring and groove assembly aligned to define said first and second positions.

43. A lyophilization device, comprising:
a top end having at least one lyophilization port axially extending upwardly, said top end defining a non-round shape;
a bottom end having generally the same shape as said top end; and
a wall portion between said top and bottom ends defining a container, said wall portion being formed from a multilaminar film including a drug compatible inner layer, an outer layer contributing substantially to the buckle strength, and a middle layer having an increased punctured resistance made of a linear low density polyethylene.

44. A lyophilization device for use with a closure, comprising:
a top end having at least one lyophilization port for a stopper;
a bottom end; and
a non-glass wall portion between said top and bottom ends defining a container, said wall portion having an inner layer of a drug compatible material bonded directly to an outer layer having a predetermined buckle strength to withstand vertical force during closure application, the cross sectional shape of said device being generally non-round wherein there are no substantial interstitial spaces when a plurality of devices are positioned in close nest array.

* * * * *